(12) United States Patent
Krishnamurti et al.

(10) Patent No.: US 11,682,495 B2
(45) Date of Patent: Jun. 20, 2023

(54) STRUCTURED MEDICAL DATA CLASSIFICATION SYSTEM FOR MONITORING AND REMEDIATING TREATMENT RISKS

(71) Applicants: Tamar Priya Krishnamurti, Pittsburgh, PA (US); Alexander Davis, Pittsburgh, PA (US); Hyagriv Simhan, Pittsburgh, PA (US)

(72) Inventors: Tamar Priya Krishnamurti, Pittsburgh, PA (US); Alexander Davis, Pittsburgh, PA (US); Hyagriv Simhan, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 34 days.

(21) Appl. No.: 16/341,736

(22) PCT Filed: Oct. 13, 2017

(86) PCT No.: PCT/US2017/056632
§ 371 (c)(1),
(2) Date: Apr. 12, 2019

(87) PCT Pub. No.: WO2018/071845
PCT Pub. Date: Apr. 19, 2018

(65) Prior Publication Data
US 2020/0051697 A1 Feb. 13, 2020

Related U.S. Application Data

(60) Provisional application No. 62/496,350, filed on Oct. 13, 2016.

(51) Int. Cl.
*G16H 50/70* (2018.01)
*G16H 50/30* (2018.01)
(Continued)

(52) U.S. Cl.
CPC .......... *G16H 50/70* (2018.01); *A61B 5/0022* (2013.01); *A61B 5/4343* (2013.01);
(Continued)

(58) Field of Classification Search
CPC ........ G16H 50/30; G16H 50/70; G16H 40/67; G16H 10/20; G06F 9/451; G06F 16/9024;
(Continued)

(56) References Cited

U.S. PATENT DOCUMENTS 6,139,494 A 10/2000 Cairnes
8,498,879 B2 7/2013 Michon et al.
(Continued)

OTHER PUBLICATIONS

Doran, G., Muandet, K., Zhang, K., Scholkopf, B. "A Permutation-Based Kernel Conditional Independence Test," Jul. 2014; http://auai.org/uai2014/proceedings/individuals/194.pdf. Accessed on Dec. 12, 2020.*
(Continued)

*Primary Examiner* — Jason S Tiedeman
*Assistant Examiner* — Aaisha Abdullah
(74) *Attorney, Agent, or Firm* — Fish & Richardson P.C.

(57) ABSTRACT

A system for classifying structured medical data, with each item of structured medical data, the system comprising a processing module that parses items of structured medical data to retrieve values of respective fields of the one or more items of structured medical data, the one or more retrieved values representing a set of medical attributes; a classification module that selects a classifier based at least one of the attributes in the set and applies the classifier to the set of attributes to classify one or more items of structured medical data into a particular risk profile; a user interface that renders one or more controls for input data that confirms one or more of the risk factors of the risk profile; and a transmitter to
(Continued)

transmit to a remote medical device, an alert that specifies confirmation of the one or more of the risk factors.

17 Claims, 7 Drawing Sheets

(51) Int. Cl.
| | |
|---|---|
| G06N 20/00 | (2019.01) |
| G16H 40/67 | (2018.01) |
| G16H 10/20 | (2018.01) |
| G06F 9/451 | (2018.01) |
| G06F 16/901 | (2019.01) |
| A61B 5/00 | (2006.01) |
| G06N 5/02 | (2023.01) |

(52) U.S. Cl.
CPC .......... *A61B 5/6801* (2013.01); *A61B 5/7267* (2013.01); *A61B 5/7275* (2013.01); *A61B 5/746* (2013.01); *A61B 5/7475* (2013.01); *G06F 9/451* (2018.02); *G06F 16/9024* (2019.01); *G06N 5/02* (2013.01); *G06N 20/00* (2019.01); *G16H 10/20* (2018.01); *G16H 40/67* (2018.01); *G16H 50/30* (2018.01)

(58) Field of Classification Search
CPC ........ G06N 20/00; G06N 5/02; A61B 5/0022; A61B 5/4343; A61B 5/6801; A61B 5/7267; A61B 5/7275; A61B 5/746; A61B 5/7475
See application file for complete search history.

(56) References Cited

U.S. PATENT DOCUMENTS

| | | | | |
|---|---|---|---|---|
| 8,756,074 | B2 | 6/2014 | Brzustowicz | |
| 8,868,436 | B2 | 10/2014 | Gotthardt | |
| 8,961,414 | B2 | 2/2015 | Teller et al. | |
| 9,110,958 | B2 | 8/2015 | Brust et al. | |
| 2006/0015372 | A1* | 1/2006 | Graham | G06Q 10/06 705/3 |
| 2006/0276707 | A1* | 12/2006 | Ya'akov | A61B 5/205 600/407 |
| 2008/0140449 | A1 | 6/2008 | Hayes | |
| 2009/0069643 | A1 | 3/2009 | Quy | |
| 2009/0070141 | A1 | 3/2009 | Jolley et al. | |
| 2009/0132275 | A1 | 5/2009 | Jung et al. | |
| 2009/0177405 | A1* | 7/2009 | Niggebrugge | G16H 50/30 702/19 |
| 2010/0004947 | A1 | 1/2010 | Nadeau et al. | |
| 2010/0177950 | A1* | 7/2010 | Donovan | G16H 50/30 382/133 |
| 2011/0245633 | A1 | 10/2011 | Goldberg | |
| 2012/0008838 | A1* | 1/2012 | Guyon | G16H 50/20 382/128 |
| 2012/0084011 | A1* | 4/2012 | Uzzo | G06F 19/00 702/19 |
| 2012/0221345 | A1 | 8/2012 | McClure et al. | |
| 2012/0270747 | A1* | 10/2012 | Elovitz | G01N 33/689 506/9 |
| 2013/0073212 | A1* | 3/2013 | Kenny | G16B 99/00 702/19 |
| 2013/0218588 | A1* | 8/2013 | Kehr | A61J 7/0481 705/2 |
| 2013/0297354 | A1 | 11/2013 | Galusha et al. | |
| 2014/0188518 | A1 | 7/2014 | Wise | |
| 2014/0279746 | A1* | 9/2014 | De Bruin | A61B 5/7267 706/12 |
| 2015/0278470 | A1* | 10/2015 | Bakker | G16H 50/30 705/2 |
| 2017/0022565 | A1* | 1/2017 | Boniface | C12Q 1/6883 |
| 2017/0124263 | A1* | 5/2017 | Crafts, Jr. | G16H 20/60 |
| 2017/0142213 | A1* | 5/2017 | Golde | G06F 8/61 |
| 2018/0011979 | A1* | 1/2018 | Zhong | G16H 10/20 |
| 2018/0011981 | A1* | 1/2018 | El Naqa | G06F 19/324 |
| 2018/0068077 | A1* | 3/2018 | Schapiro | G08B 25/005 |
| 2018/0114600 | A1* | 4/2018 | Roberts | G16H 50/30 |
| 2018/0296156 | A1* | 10/2018 | Penders | A61B 5/4356 |
| 2019/0072564 | A1* | 3/2019 | Jelliffe | G01N 33/689 |
| 2019/0137507 | A1* | 5/2019 | Patil | G06F 19/324 |

OTHER PUBLICATIONS

"Transformations to Achieve Linearity." Stat Trek, 2012. The webpage is verified as being available Mar. 5, 2012 at https://web.archive.org/web/20120305202150/https://stattrek.com/regression/linear-transformation.aspx.*

PCT International Search Report and Written Opinion in International Appln. No. PCT/US2017/056632, dated Dec. 18, 2017, 2 pages.

PCT International Preliminary Report on Patentability in International Application No. PCT/US2017/056632, dated Apr. 16, 2019, 6 pages.

* cited by examiner

STRUCTURED MEDICAL DATA CLASSIFICATION SYSTEM FOR MONITORING AND REMEDIATING TREATMENT RISKS

CLAIM OF PRIORITY

This application is a National Stage Application under 35 U.S.C. § 371 and claims the benefit of International Application No. PCT/US2017/056632, filed Oct. 13, 2017, which claims priority under 35 USC § 119(e) to U.S. Patent Application Ser. No. 62/496,350, filed on Oct. 13, 2016, the entire contents of each of which are hereby incorporated by reference.

BACKGROUND

Despite significant advances in medical interventions and healthcare delivery in the U.S., preterm births, or those that occur prior to 37 weeks of gestation, have increased by more than 30% in the past twenty-five years in the United States. Currently, more than 1 in 9 births in the U.S. are preterm. These rates are also disproportionately high among some socio-demographic groups, reaching 1 in 6 among African-Americans, with greater prevalence among families living in poverty, regardless of race.

Preterm birth is a significant life event, as it places a severe burden on the child, the mother, the family, and society. It is one of the strongest predictors of a child's survival and subsequent developmental health, as children born preterm are at much greater risk of infant death and serious morbidity in the first few weeks of life. For those who survive, there are higher chances of neuro-developmental disabilities, such as cerebral palsy, mental retardation, learning and behavioral dysfunction, and more general health problems, such as chronic asthma, poor growth, and recurrent infections. A conservative estimate of the societal cost of preterm birth in the US is $26.2 billion annually, with two of the five most expensive hospital conditions (low birth weight and respiratory distress) linked to prematurity.

The consequences of preterm birth are severe, and its causes are complex. This complexity can be seen in the wide range of risk factors identified in the research literature, including age at conception, with mothers under 16 and over 35 being particularly at risk, history of a previous preterm birth, poverty, poor weight gain, chronic and catastrophic stress, smoking, micronutrient deficiency, and genetic predisposition.

Additionally, the biological and psychosocial pathways leading to preterm birth (PTB) and other adverse pregnancy outcomes (APOs) are complex and only partially understood. It is widely believed that stress contributes to APOs including PTB, and while there are theories about the pathways underlying this association, the evidence from observational studies is mixed.

Current diagnostic approaches for preterm birth risk rely on a few distinct risk factors that are generally treated in isolation, such as taking antibiotics for asymptomatic bacteriuria or ultrasound history-indicated cerclage. However, risk factors can interact in complicated manners and seldom occur in isolation. Women with different risk profiles need reliable information about the actions that they personally can and should take to reduce their risk, not the actions that should be taken for a woman with average risk levels and typical risk factors.

Although many of these risk factors are out of the control of an expectant mother, research has identified some seemingly simple precautions with potentially significant impact, such as taking a daily multivitamin during early pregnancy. However, it has proven difficult for healthcare providers to communicate even these recommendations effectively enough to secure sustained behavior change. Few physicians and other healthcare providers have training in risk communication or access to research on how to convey these unfamiliar, and sometimes complex and uncertain, issues to patients. As a result, health care providers often fail to provide patients with information in a way that allows them to make fully informed decisions.

Even for healthcare providers who are more aware of patients' informational needs, the limited time available with each patient can prevent the in-depth discussions sometimes needed to afford patients adequate understanding. As a result, healthcare providers may use terms that patients struggle to understand, make inaccurate assumptions about patients' personal or material resources for making behavior changes, or fail to know which information should be emphasized for specific patients.

Even when provider-patient communication is good and the proper information is communicated to expectant mothers, patients face the challenge of deciding which behavioral changes are most pertinent for their own individual risk of an adverse pregnancy outcome, among the barrage of recommendations often directed at them.

Some risk factors reflect limits to women's mental models of pregnancy, leading them both to miss indicators of impending adverse outcomes (e.g., causes of bleeding, abnormal fetal movement) and to misinterpret normal development, leading to needless worry or "wasted" healthcare visits, undermining their readiness for needed ones. Such misunderstandings can be addressed by properly designed communications.

Other risk factors reflect aspects of women's lives that require not information but external support. For example, some women lack transportation to routine prenatal care, hence need help to make and keep appointments. Some women face risk of depression and intimate partner violence, and hence need proper support.

SUMMARY

This document describes systems and methods for a structured medical data classification system for monitoring and remediating treatment risks.

The classification system includes a processor; and a memory in communication with the processor, the memory storing an execution environment, the execution environment including: a processing module that parses one or more items of structured medical data to retrieve values of respective fields of the one or more items of structured medical data, the one or more retrieved values representing a set of medical attributes; a classification module that accesses the memory and selects, from the memory a classifier based at least one of the attributes in the set; where the classification module further applies the classifier to the set of attributes to classify the one or more items of structured medical data into a particular risk profile that includes a plurality of risk factors; a user interface module that generates a user interface that renders one or more controls for input of medical confirmation data that confirms one or more of the risk factors of the risk profile; and a transmission module that transmits, over one or more communication protocols and to a remote medical device, an alert that specifies confirmation of the one or more of the risk factors.

In some implementations, the alert includes an answer to a question that is customized to address a risk factor of the risk profile of the patient.

In some implementations, the classifier is generated by performing graph-learning including: receiving data representing attributes of a plurality of patients, where the attributes comprise the set of medical attributes of the patient; classifying each of the patients of the plurality of patients into one or more health outcomes; and generating a graph of nodes and edges, where a node represents an attribute, and where an edge represents a causal relationship between connected attributes. In some implementations, the patient is not included in the plurality of patients. In some implementations, the graph-learning further includes generating a set of decision trees by performing, for each decision tree of the set, operations including: selecting a subset of the plurality of patients by sampling from the plurality of patients; and selecting an attribute of the subset of the plurality of patients that splits the subset of the plurality of patients into two groups of approximately equal size; determining, using the set of decision trees, a classification of the set of attributes for the patient; and generating the risk profile of the patient based on the classification of the set of attributes for the patient.

In some implementations, the one or more risk factors include a risk of an adverse pregnancy outcome for the patient. In some implementations, the actions of the system include updating the classifier based on a reported outcome of treatment provided to the patient in response to the transmitted alert. In some implementations, the actions of the system include executing logic representing a kernel conditional independence test to the data representing the attributes of the plurality of patients; applying a linear model to the data representing the attributes of the plurality of patients; and based on application of the kernel conditional independent test and the linear model, generating the classifier. The one or more risk factors include a risk of suicide for the patient.

In some implementations, the computing device includes a wearable electronic device and where receiving the set of attributes comprises receiving physiological data from the wearable electronic device. In some implementations, the user interface displays one or more controls enabling the patient to request immediate medical attention. In some implementations, the immediate medical attention includes receiving transportation to a medical facility. In some implementations, the confirmation data comprises answers to one or more medical questions. In some implementations, the set of medical attributes comprises physiological data. In some implementations, the set of medical attributes includes data representing one or more of vaginal flora, presence of a sexually transmitted disease, lower genital tract inflammatory milieu during pregnancy, pregnancy history, race, marital status, maternal periconceptional nutritional status, pregnancy nutritional status, approximate blood alcohol level, and smoking status. In some implementations, the selected classifier is trained with attributes of other patients.

In some implementations, a method of the classification includes parsing, by a processing module, one or more items of structured medical data to retrieve values of respective fields of the one or more items of structured medical data, the one or more retrieved values representing a set of medical attributes; accessing, by a classification module, the memory and selecting, from the memory a classifier based at least one of the attributes in the set; applying, by the classification module, the classifier to the set of attributes to classify the one or more items of structured medical data into a particular risk profile that includes a plurality of risk factors; generating a user interface that renders one or more controls for input of medical confirmation data that confirms one or more of the risk factors of the risk profile; and transmitting, over one or more communication protocols and to a remote medical device, an alert that specifies confirmation of the one or more of the risk factors.

In some implementations, the alert includes an answer to a question that is customized to address a risk factor of the risk profile of the patient. In some implementations, the classifier is generated by performing graph-learning including: receiving data representing attributes of a plurality of patients, where the attributes comprise the set of medical attributes of the patient; classifying each of the patients of the plurality of patients into one or more health outcomes; and generating a graph of nodes and edges, where a node represents an attribute, and where an edge represents a causal relationship between connected attributes. In some implementations, the patient is not included in the plurality of patients, and the graph-learning further includes generating a set of decision trees by performing, for each decision tree of the set, operations including: selecting a subset of the plurality of patients by sampling from the plurality of patients; and selecting an attribute of the subset of the plurality of patients that splits the subset of the plurality of patients into two groups of approximately equal size; determining, using the set of decision trees, a classification of the set of attributes for the patient; and generating the risk profile of the patient based on the classification of the set of attributes for the patient.

In some implementations, a non-transitory computer readable medium is configured to cause one or more processing devices to perform operations including parsing one or more items of structured medical data to retrieve values of respective fields of the one or more items of structured medical data, the one or more retrieved values representing a set of medical attributes; accessing the memory and selecting, from the memory a classifier based at least one of the attributes in the set; applying the classifier to the set of attributes to classify the one or more items of structured medical data into a particular risk profile that includes a plurality of risk factors; generating a user interface that renders one or more controls for input of medical confirmation data that confirms one or more of the risk factors of the risk profile; and transmitting, over one or more communication protocols and to a remote medical device, an alert that specifies confirmation of the one or more of the risk factors.

In some implementations, the classification system includes a processor and a memory in communication with the processor, the memory storing an application which is configured to cause the smartphone to: parse one or more electronic health records to retrieve values of respective fields of the electronic health records, the one or more retrieved values associated with one or more tests performed during a pregnancy; a classification module that accesses the memory and selects, from the memory, a KCI test; where the classification module further applies the KCI test to the values of the respective fields of the electronic health records to classify a patient into a particular risk profile that includes a plurality of risk factors for adverse pregnancy outcomes; a user interface that renders one or more controls for input of answers to questions generated in response to classifying the patient into the particular risk profile, the answers confirming one or more of the risk factors of the risk profile; and a transceiver that transmits, via a mobile network, an alert that specifies confirmation of the one or more of the risk factors for an adverse pregnancy outcome.

The systems and methods enable several advantages, including several health benefits. The classification system solves a "measurement problem" associated with medical treatment. While conventional treatment systems do not collect data between visits to a physician's office, or rely on data gathered at a physician's office post-hoc, the classification system enables collection of a wide range of physiological and psychosocial attributes associated with a patient throughout a treatment process. The classification system can integrate with conventional electronic health record systems and electronic medical record systems to integrate data provided from treatment providers and data provided directly from the patients. The classification of the patient performed by the classification system and the risk profile generated for each patient enable the classification system to tailor data gathering for each patient during treatment. For example, the classification system can generate customized questions for each patient based on the data gathered for that patient at that time during a treatment process timeline. For example, the classification system can send particular questions to the patient at predetermined checkpoints during a treatment timeline (e.g., during a pregnancy) when the data gathered is particularly pertinent (e.g., to determine how the patient feels at that particular moment during pregnancy). When data are gathered from a patient (e.g., through questions answered by the patient directly to the classification system, through wearables, via a treatment provider, etc.), the classification can update a risk profile for the patient and identify high-risk situations quickly (e.g., the same day, hour, minute, etc.). An alert can be sent to a treatment provider (e.g., a physician) which includes information indicative of the high-risk situation. The alert can reduce the risk of poor treatment outcomes relative to conventional treatment timelines which rely on a patient retrospectively estimating her physiological and psychosocial status during visits to a physician.

The classification system enables early detection of physiological and psychosocial irregularities in a patient, which includes several health benefits. The data gathered during the treatment of the patient is quickly (e.g., immediately) classified with machine learning techniques that leverage data from across a patient network. The use of data from other patients having known outcomes increases the accuracy of the classification system relative to using the patient's data alone because it enables the classification system to gather more relevant data. The classification system can leverage the statistical relationships between on-invasive questions asked by the application of the classification system and the health status of patients who give the answers based on confirming the responses with actual health outcomes. For example, the classification system can determine which answers to psychosocial questions are typically indicative of a suicide risk. The classification system enables earlier detection of irregularities in the patient's attributes (e.g., data describing the patient) that suggest a risk for one or more poor treatment outcomes. For example, the classification system may determine that a patient is showing an elevated risk of suicidal thoughts, and a treatment provider can be alerted to intervene immediately. Conventional treatment systems might not detect an elevated risk for weeks, months or at all. For example, an alert can be sent to a physician that a pregnant woman is experiencing persistent high blood pressure based on data collected from a wearable apparatus, prompting questions from the classification system as to how the patient is feeling. Based on the patient's responses, the classification system can achieve early detection and immediate treatment for some pregnancy issues (e.g., preeclampsia). During conventional treatment timelines, irregularities of patient attributes (e.g., physiological or psychosocial attributes) might go undetected for weeks or months, such as only being detected during a visit to a physician's office, which can make a poor outcome more likely than that which occurs when detected immediately by the classification system based on classifications performed by the classification system. In many cases of conventional treatment, treatment is reactive rather than prospective. Irregularities of patient attributes are not detected until the poor outcome occurs, prompting a retrospective investigation as to potential causes. In some implementations, visits to a treatment provider can be more efficient than conventional systems because a problem has been identified pre-visit, resulting in cost savings and a reduced burden on the treatment provider. Early detection of elevated risks of poor treatment outcomes can reduce the need for emergency visits to treatment providers, further reducing costs.

The classification system identifies the risk factors for each patient and facilitates communication and application of remedial measures to mitigate those risks. The classification system causes increased patient engagement in care as a result of daily check-ins/recording of risk data, which may make them a) more likely to be aware of risks and/or more accurate at assessing risk b) more likely to attend routine care due to this engagement both of which will affect c) physician's likelihood of accurately diagnosing risk. The classification system causes potential costs savings (e.g., to health plans and hospitals) of early risk identification and intervention and/or increased patient engagement in care.

Additionally, the classification system provides several advantages with respect to conventional computing systems. The classification system uses a graph-learning approach rather than the use of conventional regression models. Variants on the generalized linear model, in particular, can only examine a small number of relationships in these complex, often multifactorial, medical risks. Here, the classification system applies a graph-learning algorithm approach, allowing for a big picture assessment of the stress-related risk factors to get clarity on the stress-PTB relationship. The algorithm outputs a graphical network, where a connection ("edge") between two attributes indicates either a direct causal relationship or a statistical association induced by an unmeasured variable (confounding). The graph summarizes the entire set of statistical dependencies among attributes in a dataset, and can be used to examine potential causal pathways, or identify groups of highly correlated clusters of attributes that are densely connected in the graph.

The graph-learning approach does not require the strong assumptions about the functional form of statistical dependencies used by generalized linear models, where the presence of non-linearities or interactions must be known ahead of time. Instead, a test of marginal and conditional independence is used by the classification system. The test includes a kernel conditional independence (KCI) test that can detect general statistical dependencies between attributes of interest, including non-linear associations and interaction effects. This test identifies causal relationships that are otherwise invisible in the patient data and can be applied in an ad-hoc manner. Thus, the classification system is a more flexible computing system than conventional classifiers because it can be applied to various forms of structured data sets, such as electronic health records and electronic medical records, without requiring assumptions or presuppositions about the structure or about the dependencies within the structured data sets.

In some implementations, to help reduce risks, such as the risk of adverse pregnancy outcomes, a software-based system identifies patient-specific risks from one or more data sets, and uses this information to provide particular women with the information and assistance most relevant to their personal circumstances. The information and assistance is provided via an application on a smart phone or other wireless handheld device, and is delivered when and where the woman needs it. The information can also be used to inform physicians and other medical professionals of risks to the woman.

The application can further record data and send that data to the software-based system, which uses the data to improve and refine the patient-specific risk assessments. In this way the continued use of the application increases the benefits to others using the application.

Some of the benefits that result from various embodiments of the classification system include detection of risks missed by physicians or clinical appointments, decreased risk factors arising from behavior or circumstances, providing women with medical treatments or other forms of assistance earlier than they otherwise would have received them, reduced costs in providing health care to the women, a reduction in adverse birth outcomes, and a reduction in poor health outcomes for the fetus after birth.

The details of one or more embodiments of the classification system are set forth in the accompanying drawings and the description below. Other features, objects, and advantages of the classification system will be apparent from the description and drawings, and from the claims.

DESCRIPTION OF DRAWINGS

Like reference symbols in the various drawings indicate like elements.

DETAILED DESCRIPTION

Figure 1:
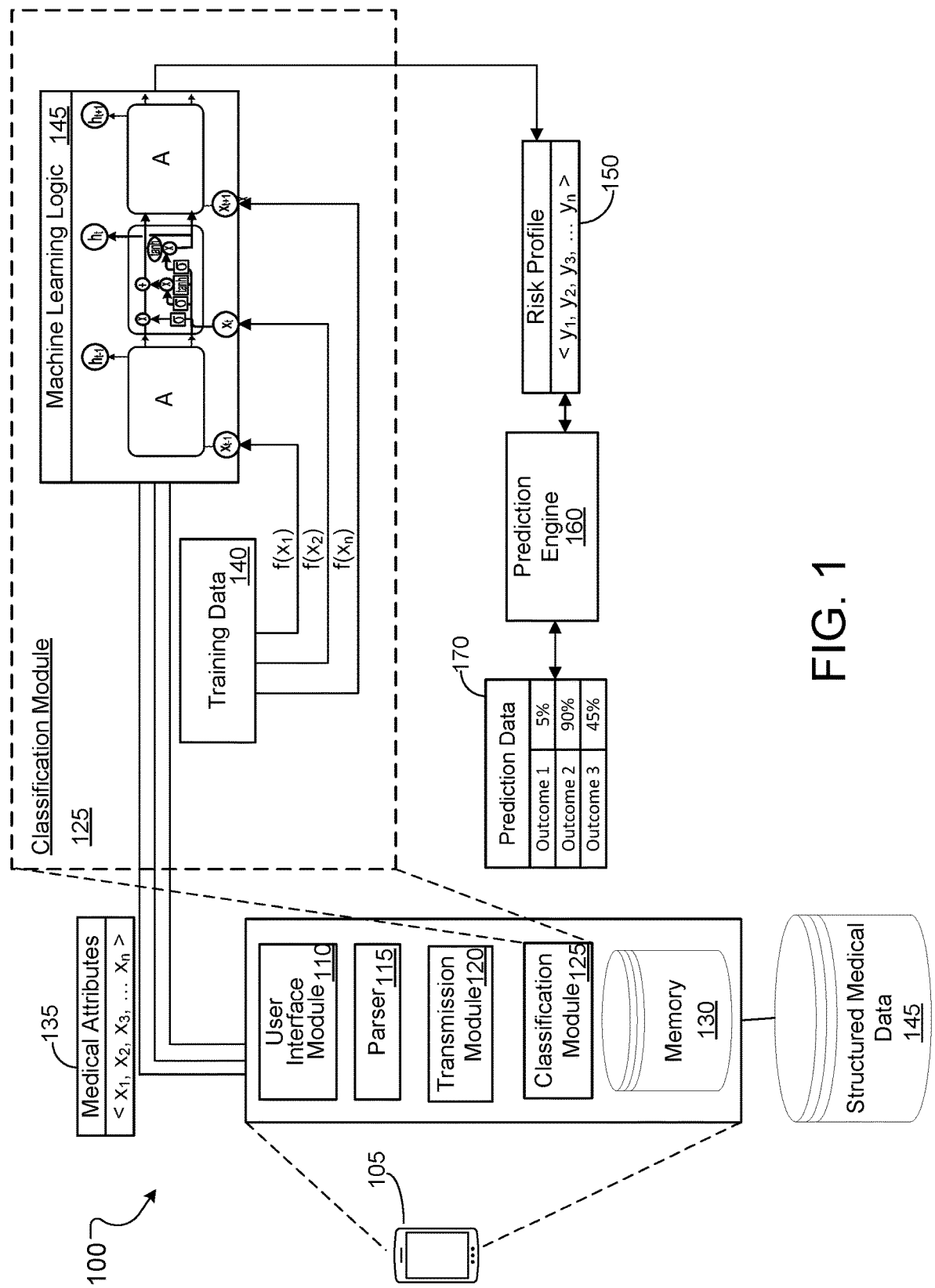
FIG. 1 depicts a block diagram of the classification system.

FIG. 1 shows an example of the classification system 100. The classification system 100 includes a classification module 125 and a prediction engine 160. The client device 105 is configured to display to the patient, such as by a user interface module 110, a user interface with which a user can interact. Examples of the user interface are described in relation to FIGS. 2-3. The user interface provides a feedback mechanism for the patient (e.g., the user of the classification system 100). The classification system 100 processes these inputs to determine features (e.g., attributes) that are indicative of the user's interaction (e.g., answers or data) with the user interface module 110. The client device 105 can retrieve user data from a structured medical data 145 database, such as demographic data, etc., which can be input into the parser 115 to determine the attributes of the data.

The interactions with the interface are represented by the attributes of a set of medical attributes 125. The set of attributes concisely represents the characteristics of the interactions/data for a particular user, and can be processed by the classification module 125, such as using a neural network or other machine learning (e.g., graph learning as described in further detail below). The set of medical attributes 125 is generated using parser 115. The parser 115 reads the inputs of selected controls (or of measured data, such as wearable electronic data, such as described below) and transforms the raw input data into a formatted vector that represents the attributes of a patient.

The set of medical attributes 125 is sent from the client device to the classification module 125 of the classification system 100. The classification module 125 include logic that transforms the set of medical attributes 125 into feature risk profile 150 that can be used to make predictions for dyslexia for the user by the prediction engine 160. The feature classification engine includes a feature transform logic engine 135 and classification module 125.

The classification system prepares the set of attributes 135 as inputs for the classification module 125. For example, the feature transform logic 135 can normalize the features of the set of medical attributes 135 to values that can be recognized by the classification module 125, such as activation inputs for a neural network. In some implementations, the machine learning logic is a support vector machine. In some implementations, the features of the feature vector are transformed into values between 0 and 1 through a non-linear transformation, where the normalized value represents an activation level for the neural network, and where the normalized scale is a non-linear representation of the values of the features before the normalization process. The values to which the features are transformed can depend on a type of machine learning logic being used, and the weighting scheme associated with the machine learning logic.

The classification module 125 (e.g., a neural network, support vector machine, etc.) receives the normalized features of the set of medical attributes 125 and computes risk profile 150, such as through a graph-learning process described in greater detail below. For example, neural network logic can include a long short-term memory neural network, which tracks dependencies between features of the set of medical attributes 135. Other recurrent neural networks can be used. Other machine learning classifiers can be used as well.

The classifier can be selected by the classification module based on an identity of one or more of the attributes of the set of attributes 135. For example, if the patient is determined to be a woman who is pregnant, a pregnancy classifier can be selected for performing graph-learning operations on the attributes 135. The classifier and training data 140 can be selected in advance of the graph-learning process to front-load processing and reduce latency times for sending alerts to treatment providers.

The feature classifier data 150 includes classification metrics for one or more of the attributes of the set of medical attributes 135 to values for known health outcomes, such as from an attribute library.

In some implementations, the classification metric values can be stored in a feature index. The index shows the classification values for each feature of the index. The prediction engine 160, using the classification values, generates prediction data 170 representing one or more prediction values for various health outcomes based on the risk profile 150. If a prediction value is above a predetermined threshold, the prediction engine 160 predicts that the patient will have the health outcome, and an alert is generated and transmitted by the transmission module 120 for sending to a treatment provider, prompting the provider to intervene. For example, the predetermined threshold can be a prediction value above 50%. In some implementations, to reduce false positives or false negatives, the predetermined threshold can be a higher percentage or a lower percentage than 50%.

The transmission module 120 sends the alert to a treatment provider, such as a physician, hospital system, police officer, emergency hotline, etc. The alert can be sent immediately (e.g., in real-time or near real-time) when a poor health outcome is predicted. In some implementations, the alert can be sent as an email message, phone call, SMS message, etc. The alert can include information describing the predicted health outcome to the physician. In some implementations, the alert can include an automatic scheduling of a visit to the physician's office, recommend further testing to be run, and so forth in order to increase the efficiency of treatment to the patient.

In some implementations the client device 105 includes a wearable electronic device. The wearable device monitors one or more health attributes of the patient, such as heart rate, blood pressure, body temperature, etc. In some implementations, wearable device data can be used by the classification module 125 to prompt further questioning to the patient via the user interface module 110 in order to determine whether the patient is at risk for a poor health outcome. For example, if a patient is determined to have an elevated heart rate for a period of time, the patient can be prompted to answer questions regarding whether the patient is anxious or otherwise at risk of a health issue.

The graph-learning algorithm of the classification module 125 constructs a graph that shows statistical dependence relationships not explained by other attributes using a systematic series of independence tests. It begins by connecting all attributes (represented as nodes or vertices in the graph), then removes the connection between attributes if they are marginally independent; that is, the attributes are not associated, ignoring other attributes as mediators. For example, in a dataset containing age, income, and insurance type of pregnant women, we would expect all three attributes to be pairwise marginally dependent, meaning they would all be connected in the graph after the first iteration of the algorithm. In the next step, the algorithm sequentially controls for other sets of attributes that could explain the dependence. If two attributes that were initially connected after testing for marginal dependence become independent after controlling for one or more other attributes, the edge between that pair of attributes is removed. For example, the algorithm will show age and insurance type as independent after controlling for income, because age is independent of insurance type once income is considered. The edges between attributes that remain at the termination of the algorithm is a graph of attributes that are connected only if they are marginally dependent and remain dependent after controlling for all other attributes.

The test of independence is KCI, which relies on mathematical structures called reproducing kernel Hilbert spaces that, under weak conditions, can be used to test for general dependence between two attributes, as well as test for conditional dependence when there are covariates. The intuition behind the KCI test is to construct a correlation test between two attributes allowing each variable to take on any smooth transformation, such as a polynomial transformation. If the two attributes are uncorrelated under all transformations, they are statistically independent.

Because KCI tests are computationally intensive, and the graph-learning algorithm involves many KCI tests, several approaches can be used to reduce processing times. Specifically, the marginal independence of each pair of attributes is first tested using a correlation-based test. If the correlation-based test is significant, the edge between the attributes is retained. If the test is not significant, a KCI test is used. Because dependence as measured by correlation implies dependence as measured by KCI, the approach should pick up, at minimum, the same associations. However, the requirement that KCI is conducted in a subset of tests significantly increases the speed of the algorithm and reduces a processing time of the classification system 100, reducing a time delay of sending an alert if necessary.

Some patients can be missing information for specific attributes. Because the algorithm performs a series of distinct tests, each requiring different sets of attributes, each test used the complete observations for the attributes it required. As a sensitivity analysis, we used two approaches: (1) include only patients with complete data across all attributes (n=297), (2) randomly imputing missing data.

In some implementations, an application or other software installed on a smartphone or other handheld device facilitates the collection of data that can indicate preterm birth risk and/or other risks to a woman, such as risk that delivery by caesarean section will be required in the current birth and/or future births by the woman, risk of depression, risk of poor sleep, and risk of domestic violence. Alternatively, or additionally, the smartphone can reduce or assist in reducing such risks, e.g., by providing the woman with information such as behavioral recommendations, by providing the woman with access to resources such as rides, or by contacting physicians, other medical professionals, or others to alert them to the woman's risks or need for assistance. Moreover, in some embodiments the application can reduce or assist in reducing such risks to a woman through use of an individual risk profile for that woman.

In some embodiments, the functions performed by an application or by software installed on or operating via a smartphone or other handheld device may be performed by other devices such as by a web server that communicates with one or more individuals (e.g., pregnant women, physicians, other medical professionals) via a web browser or similar interface.

According to an embodiment, a computer system creates an individual risk profile for woman based on the woman's particular characteristics. Therefore, two women with different characteristics could have different individual risk profiles. The individual risk profile is useful in providing information to the woman as well as to others who assist in her care and treatment. For example, the individual risk profile can be received by a smart phone used by the woman, and the smart phone could use the individual risk profile to determine various recommendations to provide to the woman and how generally to interact with the woman.

To permit the creation of individual risk profiles that are based on particular characteristics, one embodiment of the classification system 100 includes the creation of a classifier. The classifier predicts, based on a set of values of predictor attributes for a woman, whether the woman is at risk for preterm birth, and/or how likely the woman is at risk for preterm birth. The classifier can be created by learning from a set of training data which values of certain predictor attributes indicate a risk of preterm birth.

The classifier may also be designed to make other classifications besides the risk for preterm birth. For example, the classifier may be designed to make classifications of the woman's risk of domestic violence, drug abuse, depression or other mental health conditions, sleep problems, pregnancy-related medical conditions such as gestational diabetes and fetal distress, delivery related conditions such as the risk that delivery by caesarean section will be required in the current birth and/or future births by the woman, and infant-related risks such as sudden infant death syndrome, allergic reactions, breastfeeding, and failure to thrive.

In some implementations, instead of or in addition to classifying the risk of the woman experiencing some type of event in the future (e.g., experiencing a preterm birth), the classifier can be designed to classify whether the woman has already experienced that type of event. For example, the classifier can be designed to classify whether the woman has already experienced domestic violence, drug abuse, or any of the other risks described herein. In some implementations, the classifier includes a set of classifiers. For example, different classifiers can be designed to indicate different risks, and/or to predict risks from different sets of predictor attributes, and/or to predict risks from different values of predictor attributes. In some implementations, the results of different classifiers can be combined in various ways to make predictions. The training set may include various data. One type of training set includes data on a set of women. Each woman in the training set is classified as either having given birth preterm or having given birth at term. Moreover, for each woman in the training set there are a set of values of predictor attributes, notwithstanding this terminology, a predictor variable may or may not actually be useful in predicting the classification of a woman, though it is anticipated that many of the predictor attributes will actually be useful in predicting the classification.

Many different types of predictor attributes can be used in different combinations. Some types of predictor attributes include biochemical/clinical predictors (e.g., cervicovaginal fetal fibronectin, transvaginal ultrasound assessment of cervical length), historical and obstetrical factors (e.g., history of prior preterm birth, history of prior term birth), demographic features (e.g., race, marital status), psychological stress, psychosocial measures and behavioral measures.

In some implementations, the set of predictor attributes includes some or all of the following: cervicovaginal fetal fibronectin, transvaginal ultrasound assessment of cervical length, vaginal flora, sexually transmitted diseases (STDs), lower genital tract inflammatory milieu during pregnancy, whether the woman has ever given birth before, history of prior preterm birth, history of prior term birth, race, marital status, maternal periconceptional nutritional status, pregnancy nutritional status, environmental exposure, childhood trauma, psychosocial factors, drug or alcohol use, child's paternal medical history, and smoking.

Many types of classifiers may be created to predict, based on a woman's set of values of predictor attributes, whether that woman is at risk for preterm birth. In some implementations, a decision tree is trained to create such a classifier. In another embodiment, a set of decision trees are created to collectively form a classifier. The following is one way of creating a set of decision trees from a given training set.

For each of the decision trees to be created, a subset of the women in the training set is created by randomly sampling with replacement from the training set. A number m that is less than or equal to the number of predictor attributes is selected. Then, nodes in the decision tree are iteratively created by selecting a random subset of m predictor attributes, and selecting the predictor variable from the subset that best splits the node in the decision tree, for the given subset of the women. In other words, the predictor variable is selected such that the node maximally separates women who have had and have not had preterm births. The node is then split with that predictor variable, which creates child nodes and each child node is responsible for some portion of the training set split by the parent node. Therefore, the first (root) node of the tree will split based on the predictor variable (out of the m predictor attributes selected) that best predicts preterm birth. This process is repeated iteratively on the child nodes until nodes can no longer be split, nodes pertain to too few samples, or some other stopping criteria. Each iteration results in a progressively more complex tree.

Once all the decision trees have been created, each decision tree is used to classify one or more women not in the training set. Specifically, for each of these woman every decision tree is used to determine a respective classification of a set of values of predictor attributes. For each woman, the majority vote of all classifications for that woman by all decision trees is taken to determine the final classification for the woman. In this manner, the predictions of the individual trees are averaged or otherwise combined, producing an aggregate tree that typically makes better predictions than any single tree.

Once a woman has been classified as either at risk for preterm birth or not, and individual risk profile for the woman can be created. In some implementations, some values of predictor attributes for a particular woman, if changed, would decrease the risks of preterm birth. This potential to decrease risk by changing the values of one or more predictor attributes can be ascertained by classifying an altered set of values of predictor attributes (i.e. the set of values the woman would or could have if changes were successfully made). If the classification of the altered set shows a lower risk of preterm birth, then the change may be advisable.

Some of the predictor attributes, such as whether the woman has previously given birth, cannot be altered by the woman. Other predictor attributes, such as taking daily vitamins and smoking, can be altered. Recognizing these two types of predictor attributes leads to different types of available treatment options. Some treatments can be designed to try to change the value of a predictor variable (because it is capable of being changed), while other treatments, such as greater supervision and testing, can be triggered by the values of certain attributes but are not designed to change the values of those attributes.

The risk profile is transmitted to the woman's smart phone, which runs an application designed to perform various methods described herein. The smart phone then can utilize the individual risk profile in interacting with the woman to reduce or assist in reducing risks that she faces. The smart phone can provide information to the woman in a clear, credible, authoritative, form to help the women implement needed actions. In general, the smart phone can interact with the woman in various ways to provide information and services to the woman, and to collect data from the woman. Some of the data that is collected can be used to indicate increases (or decreases) in preterm birth risk and other risks the woman faces. As described above, in different embodiments of the classification system, one or more different kinds of risks are evaluated.

Figure 2:
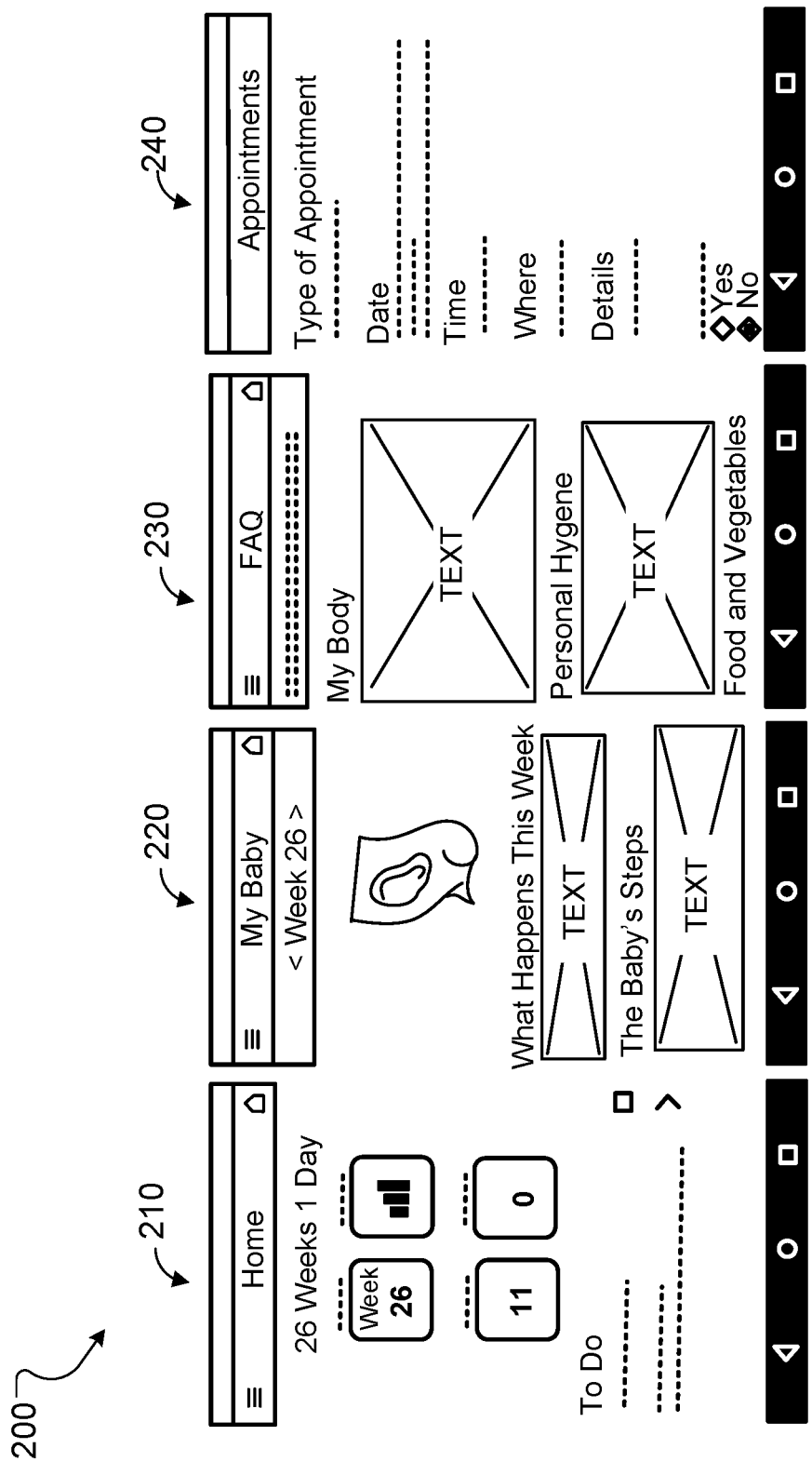
FIGS. 2-3 depict examples of screens displayed by an interface of the classification system.

FIG. 2 depicts several examples 200 of screens (the content and controls displayed by a user interface) that could be presented to the woman using the application. A home screen 210 displays general information and general tasks to perform. A screen 220 displays pregnancy related education, in particular education on the state of a fetus at the twenty sixth week. A screen 230 displays a set of frequently asked questions, the answers to which are available upon request by selecting the question. A screen 240 displays a tool that enables the woman to schedule an appointment for an ultrasound examination.

Voluntary assessments are one way of collecting data that can indicate such risks. In one type of voluntary assessment, a series of questions are presented to the woman via the smartphone (e.g., as text on the screen of the smartphone) and the woman submits responses to those questions via the smartphone (e.g., by selecting from multiple choice questions by pressing the touchscreen of the smartphone).

Some assessments can be conducted periodically (e.g., daily, weekly). Alternatively, some assessments can be conducted based on other factors such as the woman's phase of pregnancy. Alternatively, some assessments can be conducted in response to a determination by the software (e.g., based on the woman's answers to previously-administered questions, based on information from medical tests) that the woman faces, or potentially faces, an elevated risk. In one embodiment, a woman may take a voluntary assessment, and the responses to one or more questions in the assessment can indicate that the woman might have a greater risk. In one embodiment, a sequence of increasingly-specific questions can elicit from the woman a sequence of responses that indicate an elevated risk.

For example, a sequence of questions may begin by asking the woman's mood, and the woman responds that she is in a poor mood. Then a sequence of questions progressively probes the reasons for the poor mood. For some risks, a pattern of such a mood or a pattern of consistent answers for the woman's reasons for her poor mood are relevant, so these patterns are solicited by conducting appropriate assessments periodically and the answers are assessed to detect a pattern. If the responses indicate that the woman's reasons for a poor mood relate to a risk of intimate partner violence, the software informs the woman of her risk, provides the woman with suggested actions she should take, and/or sends a message to alert the woman's physician to this risk.

Figure 3:
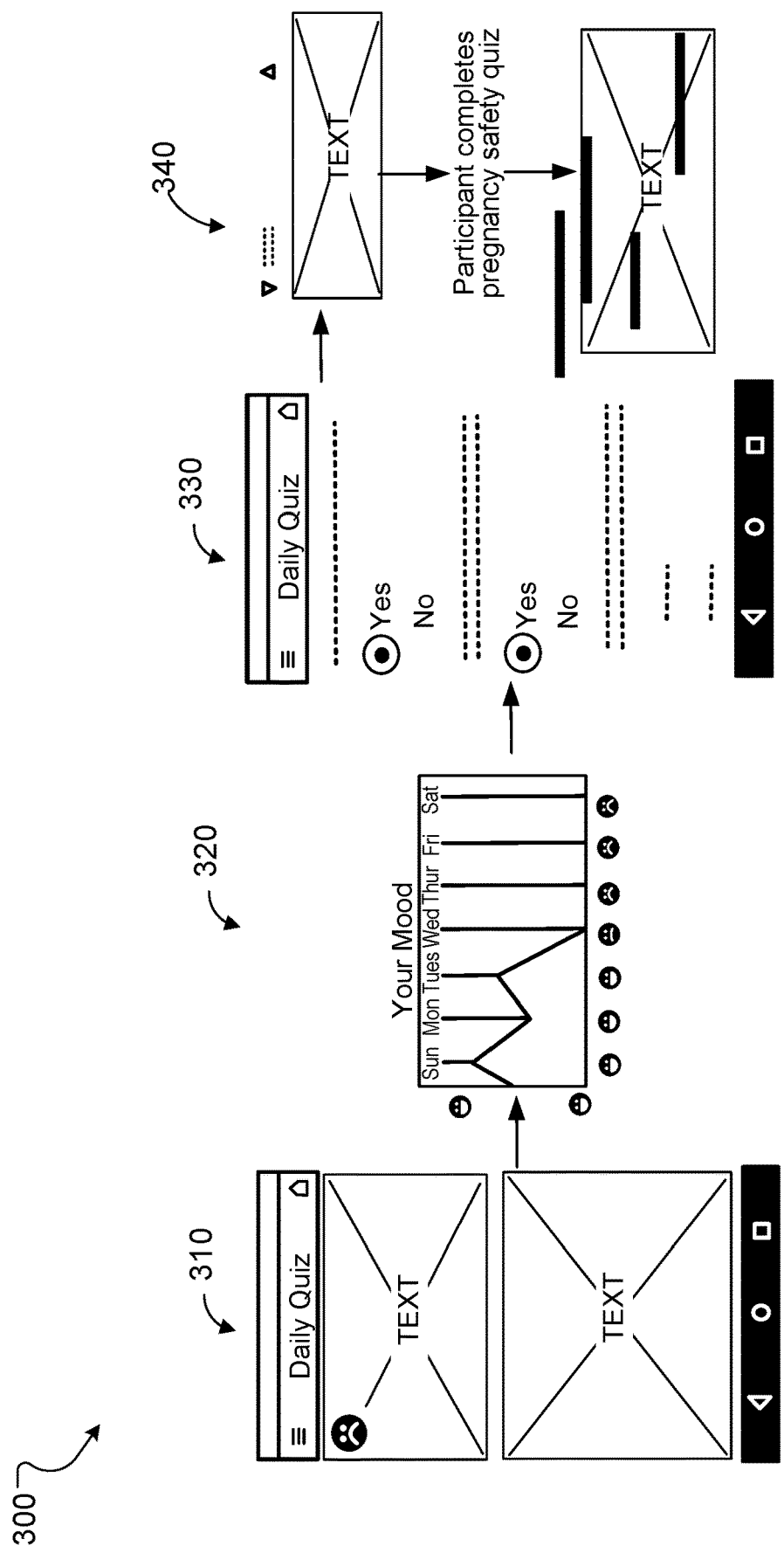

FIG. 3 depicts several examples 300 of screens (the content and controls displayed by a user interface) that could be presented to the woman using the application to conduct an assessment.

A screen 310 allows the woman to input her mood and primary influence on her mood. A screen 320 displays the recorded history of the mood of the woman over a period of time. The software displays screen 330 in this example because the woman's responses to previous questions indicate that the woman might have a greater risk. Therefore, screen 330 provides a sequence of increasingly-specific questions to elicit from the woman a sequence of responses that indicate an elevated risk. The responses indicate that the woman's reasons for a poor mood relate to her feeling unsafe, so screen 340 directs her to take an assessment to determine her safety. The results of this assessment indicate an elevated risk of intimate partner violence, so screen 350 displays a message to the woman's physician indicating this risk.

In some implementations, the application on the smart phone can provide a user interface that allows the woman to input, and receive feedback on, pregnancy related information. For example, the application can provide an interface that allows the woman to count, and input the count, of fetal kicks and contractions.

The application on the smart phone can provide a user interface that allows for other types of interaction with the woman. In some implementations, the woman can request educational information or other information. For example, the application can be designed to permit the woman to request (and be provided with) certain kinds of pregnancy related information, such as feedback on diet, lifestyle, or other behavioral decisions. In some implementations, the woman can use the application to create appointments with medical providers (e.g., physicians, medical technicians) or with other service providers. In some implementations, the woman can request a service such as a ride, e.g., to drive the woman to an appointment. In some implementations, the application can be designed to permit the woman to provide information on her behavior or her outcomes, such as her feelings of preparedness, depression, daily vitamin use, clinic attendance, and stress (whether pregnancy-related or otherwise). The application can also collect information on the woman's engagement with and use of the application and other behavior. Various other inputs can be collected from the woman.

The application on the smart phone can provide a user interface that allows for other types of services to be provided. In some implementations, the application can provide nudges to urge the woman to take certain actions (e.g., attend an appointment), engage in certain behaviors (e.g., take vitamins daily), or refrain from certain behaviors (e.g., smoking). In some implementations, the application on the smart phone can communicate with physicians, healthcare providers, or others. Such communication may be requested by the woman via the smartphone, or can be initiated by the smart phone without being requested by the woman. For example, if the application determines (e.g., based on received responses to questions presented via the app) that the woman faces a risk such as risks from clinical indicators (e.g., preterm contractions), intimate partner violence, or suicidal ideation, the application can contact the woman's physician or others to alert them to the woman's risks or need for assistance.

The application can also provide various data it collects to physicians, through operational and electronic integration with clinical care infrastructure and additionally, e.g. via a web interface that allows the physicians or others to access information on a particular woman, or aggregate information on a set of women (either with or without personally identifying information).

In some implementations, additional information can be collected and used to further refine or redefine the classifier. One such type of additional information is information that is collected from the smart phone application. As a woman uses the smart phone application to reduce or assist in reducing preterm birth risks, the application collects information volunteered by the woman, such as patterns of behavior she has engaged in (e.g., vitamin use), events she has experienced, her mood at different times, and whether she has attended medical or other appointments.

Such information volunteered by the women may be generated in the form of responses to voluntary assessments conducted by the application. Thus, the application can be used to collect desired information from women, and this information may be utilized, e.g., to further improve the classifier or to test potential improvements. If one type of information is believed or suspected to be useful in predicting the risk of preterm birth, then that type of information can be directly or indirectly requested of women using the application. In this manner the application can collect (e.g., in real-time) one or more new predictor attributes that were not included in the original set of predictor attributes.

Some other predictor attributes that can be included in the original set of predictor attributes or in the new set, include depression (e.g., using the Edinburgh depression scale), daily vitamin use, accessing of resources provided by the app, use of the app, appointment attendance, subjective mood, and levels of stress.

Once information is received from one or more smartphones, this information can be considered to be a second training set that includes a set of values of predictor attributes for each woman in the second training set. At some point after the woman gives birth (term or preterm), this information is recorded and associated with the corresponding values of predictor attributes for the woman. This information constitutes a classification of the woman, so this second training set can be used (alone or with the original training set) to create a second set of decisions trees. Alternatively, other data besides preterm birth outcome, e.g., mortality, birth weight, neonatal intensive care unit admittance, can be used for classification.

Figure 4:
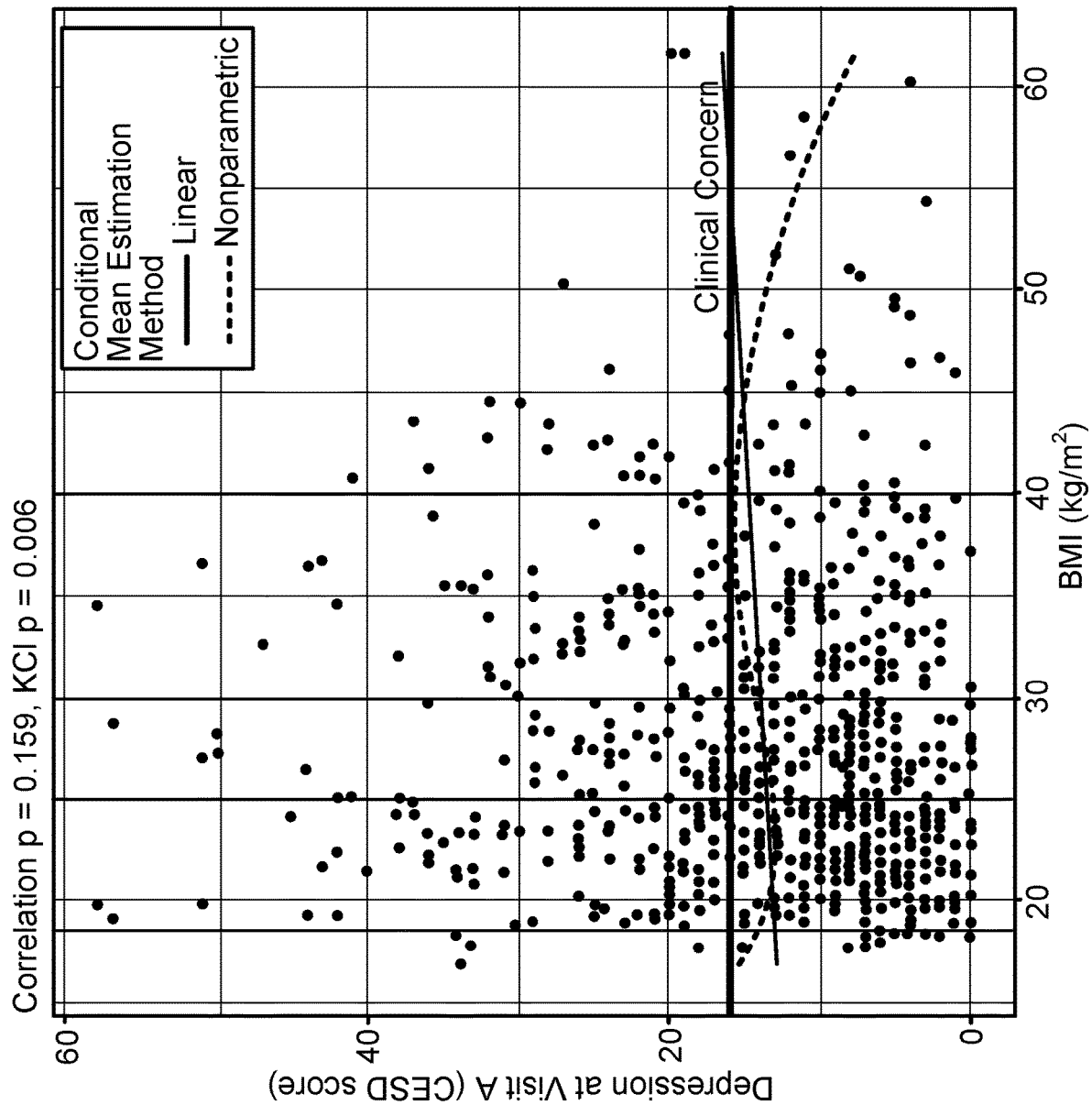
FIG. 4 depicts classification results.

As an example, FIG. 4 includes results data 400 that shows the relationship between body-mass index (BMI) and depression at visit 1 among women in a Measures of Maternal Stress (MOMS) study, where a generalized linear model would be unlikely to pick up the non-linear pattern. KCI can pick up statistical dependence even when the mean of one variable is not related to the levels of the other, for example if the variance of one variable is related to the other (sometimes called heteroscedasticity). The independence test we use in the paper will detect any form of statistical dependence, provided enough data are available. For example, duration of gestation is thought to be shorter for women with high and low BMI and longer for women with a normal BMI; using KCI can ensure that associations such as this will not be missed as frequently as it could be with a correlation-based test. Table 1 details the capabilities of the graphical approach in contrast with generalized linear models.

TABLE 1

Application of graph-learning versus regression

| | Benefits | Limitations |
|---|---|---|
| Regression (generalized linear model) | Quantifies association while controlling for other attributes<br>Some regression techniques can detect proximal causes (penalized regression) | Cannot show pathways through attributes<br>Not good at nonparametric variable selection<br>Requires imputation/deletion of missing data |
| Graph-learning | Shows pathways<br>Shows clusters of attributes (groups of highly associated attributes)<br>Can be non-parametric<br>Variable selection is easy to see<br>Uses as much data as possible | Cannot quantify probability of being correct<br>Multiple testing (simultaneous statistical inferences)<br>Slow analysis |

To demonstrate the approach, we apply a graph-learning algorithm to data from the Measures of Maternal Stress (MOMS) study, an observational prospective cohort study of 744 nulliparous mothers recruited from 4 major US hospitals. The data consists of adverse pregnancy outcomes and maternal attributes including (1) maternal stress measures, such as responses to psychometric questionnaires and stress biomarkers, and (2) key factors, such as immunologic biomarkers, demographics, and medical history.

As with any analytical tool, the graph-learning approach has its limitations. First, because no test of statistical independence can definitively separate causation from confounding, interpreting the connections between attributes in the graph as definitively causal runs the risk of false positives (or, conversely, the absence of connections could be false negatives). Second, KCI is relatively slow to compute, especially when there are many attributes that must be conditioned on (controlled for), or if there are many observations. An approach that mixes linear tests with KCI can be implemented to maintain tractability.

In an example, in the Measure of Maternal Stress (MOMS) study, 744 women were recruited at Children's Hospital of Philadelphia, Northwestern University Hospital, University of Texas Health Science Center Antonio, or University of Pittsburgh Medical Center between 2013 and 2015. All women were at least 18 years of age with a singleton intrauterine pregnancy, less than 21 weeks pregnant at enrollment, English-speaking, and with no known fetal congenital anomalies. Enrolled women were examined twice, between 12 and 21 weeks of gestation (visit A), and between 32 and 36 weeks of gestation (visit B). The study included post-delivery medical records such as pregnancy outcomes. Table 2 summarizes demographics, study settings, and selected adverse pregnancy outcomes in the MOMS study.

TABLE 2

Attributes of women in the Measures of Maternal Stress (MOMS) study

| | |
|---|---|
| Subjects | 744 |
| Age at enrollment, mean(IQR) years | 29 (25,33) |
| Race | |
| Black | 127 (17%) |
| Hispanic | 145 (20%) |
| Non-Hispanic White | 145 (58%) |
| Other | 39 (5%) |
| Income | |
| <$15k | 108 (16%) |
| $15k-$50k | 221 (33%) |
| $50k-$100k | 193 (29%) |
| >$100K | 146 (22%) |
| BMI (kg/m) | 26 (22, 32) |
| Hospital | |
| Children's Hospital of Philadelphia | 175 (24%) |
| Northwestern University | 191 (26%) |
| University of Pittsburgh | 200 (27%) |
| University of Texas Health Science Center at San Antonio | 178 (24%) |
| Current Smoker | 76 (10%) |
| Prior Preterm Births | |
| 0 | 323 (44%) |
| 1 | 366 (49%) |
| 2 | 51 (7%) |
| Education | |
| Refused to answer | 1 (0%) |
| High school or less | 198 (27%) |
| Some college or associates degree | 254 (34%) |
| Bachelor's degree or more | 289 (34%) |
| Preeclampsia | 36 (5%) |
| Preterm births | 57 (8%) |

The study collected demographic information (age, race, income, marital status, etc.), medical history (prior preterm births, history of cancer, diabetes, heart disease, etc.), inflammation, infection, and stress biomarkers (CRH, cortisol, glucocorticoid sensitivity, C-reactive Protein, Epstein- Ban virus antibodies, cytokines/chemokines), and responses to stress-related psychological questionnaires (Childhood Trauma, Abuse Assessment Screen, Social Problems, Questions about Your Childhood, Perceived Stress Scale, Prenatal Distress, Williams Discrimination Scale, Medical Outcomes Study, Social Support Survey, Rosenberg Self-Esteem Scale, Center for Epidemiological Studies—Depression Scale, Sleep Quality Index, Sarason's Life Experience Survey).

The MOMS study was designed to test the following hypotheses about the relationship between stress and adverse pregnancy outcomes: H1: Elevated cortisol very early in pregnancy is associated with preterm birth. H2: Elevated C-reactive protein (CRP) is associated with preterm birth. H3: Antibody levels of Epstein Barr Virus (EBV) are associated with APOs, including shorter durations of pregnancy. H4: Cytokine and chemokine markers of inflammation are associated with psychosocial stressors and linked with maternal health.

Figure 5:
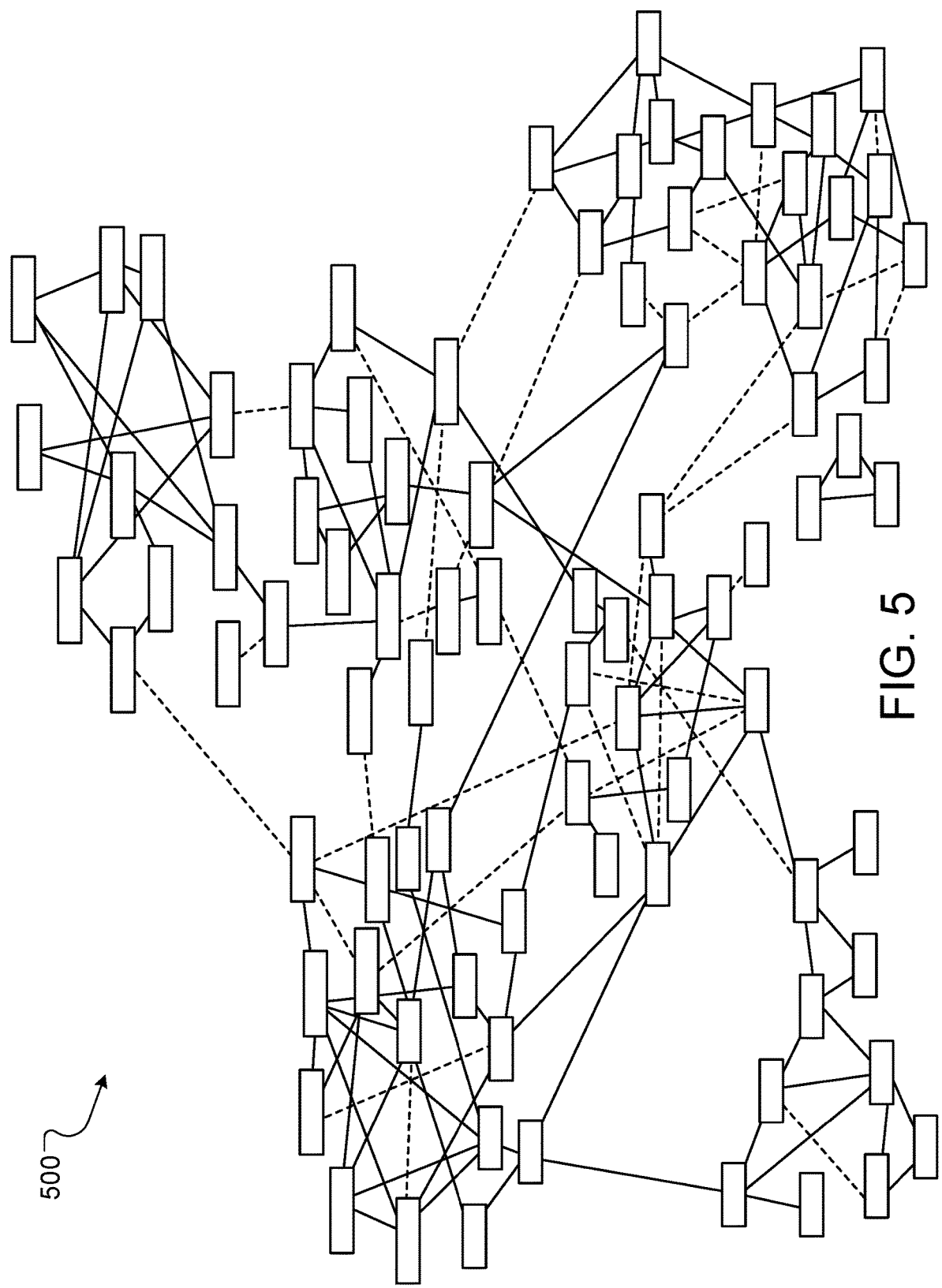
FIG. 5 depicts a graph including nodes patient attribute data and edges of associations between the nodes.

FIG. 5 shows an example graph 500 that results from the graph-learning algorithm for detecting adverse pregnancy outcomes (APOs). The interpretable features of the graph are clusters of attributes, direct links to APOs, and pathways to APOs. Clustering is characterized by a high degree of connections between groups of attributes, with relatively few connections to attributes outside the cluster. From a qualitative assessment, in the example graph 500, there are approximately 7 clusters of attributes: (1) self-reported trauma (sexual abuse, physical abuse, emotional neglect, domestic abuse), (2) stressful life events, (3) inflammatory biomarkers (interleukin 6, 10, TNF alpha, IFN gamma), (4) stress biomarkers (CRH, cortisol), (5) demographics (age, income, insurance type, education, race), (6) self-reported psycho-social factors (perceived stress, depression, discrimination, social support, self-esteem) and (7) adverse pregnancy outcomes (weeks of gestation/PTB).

Several clusters of attributes are sparsely connected to other clusters. The stressful life events survey (SLES) responses, inflammation biomarkers, trauma, and psychosocial factors are all highly interconnected internally. The attributes within compact clusters tend to predict each other rather than APOs. This indicates that, for identifying pregnancies at risk of APOs, few if any of them will be of direct value clinically. For the narrow goal of predicting APOs, the unconnected attributes could be dispensed with, reducing data collection burdens in the future. There are several instances where attributes connect directly to APOs. The SLES subject score at 32-36 weeks for events reported during the pre-pregnancy period is connected to preeclampsia. The IL6/IL10 ratio at 32-36 weeks is connected to pregestational diabetes.

The Williams discrimination total score was connected to gestational diabetes. Hair cortisol at 12-21 weeks of gestation (visit A) is connected to preeclampsia and pregestational diabetes. Examination of the algorithm output showed that hair cortisol at 32-36 weeks of gestation (visit B) was also connected to hair cortisol at 12-21 weeks until conditioning on pregestational diabetes. This suggests that gestational diabetes influences hair cortisol.

Questionnaires on prior trauma such as emotional neglect, domestic abuse, physical abuse, childhood trauma, sexual abuse, and emotional abuse as a cluster are only connected to the rest of the graph through childhood disadvantage and emotional neglect. This suggests that this cluster of questionnaires gives little information for predicting adverse pregnancy outcomes, except for sleep quality and social support.

Inflammation biomarkers including interleukins, interferon gamma, C-reactive protein (CRP), and tumor necrosis factor alpha attributes are clustered and sparsely connected to other clusters, but have no direct pathway to adverse pregnancy outcomes. CRP is associated with sleep quality, as noted in recent research (cite) but does not link to any APOs. The graph suggests that Epstein-Barr virus is only associated with other attributes through its association with age, making it unlikely to affect any APOs. Hair cortisol 12-21 weeks is connected to preeclampsia and pregestational diabetes. Examination of the series of hypothesis tests showed that hair cortisol at 32-36 weeks was also connected to hair cortisol at 12-21 weeks until conditioning on pregestational diabetes. This likely suggests that gestational diabetes influences hair cortisol.

The APOs tended to cluster among themselves. Weeks of gestation (PTB) is connected to preeclampsia, gestational hypertention, gestational diabetes, and pre-gestational diabetes (all potential causes), as well as the number of days the baby stays in the hospital and adjusted birth weight (potential effects). While many other attributes have a marginal association with weeks of gestation, all can be explained by these six attributes.

The attributes connected to preeclampsia are change in CRH between visits adjusted for gestational age, hair cortisol at 12-21 weeks, gestational hypertension, and weeks of gestation. Further, several CRH attributes (CRH at 12-21 weeks and 32-36 weeks, Change in CRH between visits adjusted for gestational age) are clustered together and connected to preeclampsia.

The example graph 500 shows that only 6 of the 74 stress attributes measured are directly connected to adverse pregnancy outcomes. SLES prepregnancy subjective score at 32-36 weeks is connected to Preeclampsia. SLES objective score at 32-36 weeks is connected to the number of days in the neonatal intensive care unit ("Baby days in hospital"), and IL6/IL10 ratio at 32-36 weeks is connected to Pregestational diabetes and Race.

Figure 6:
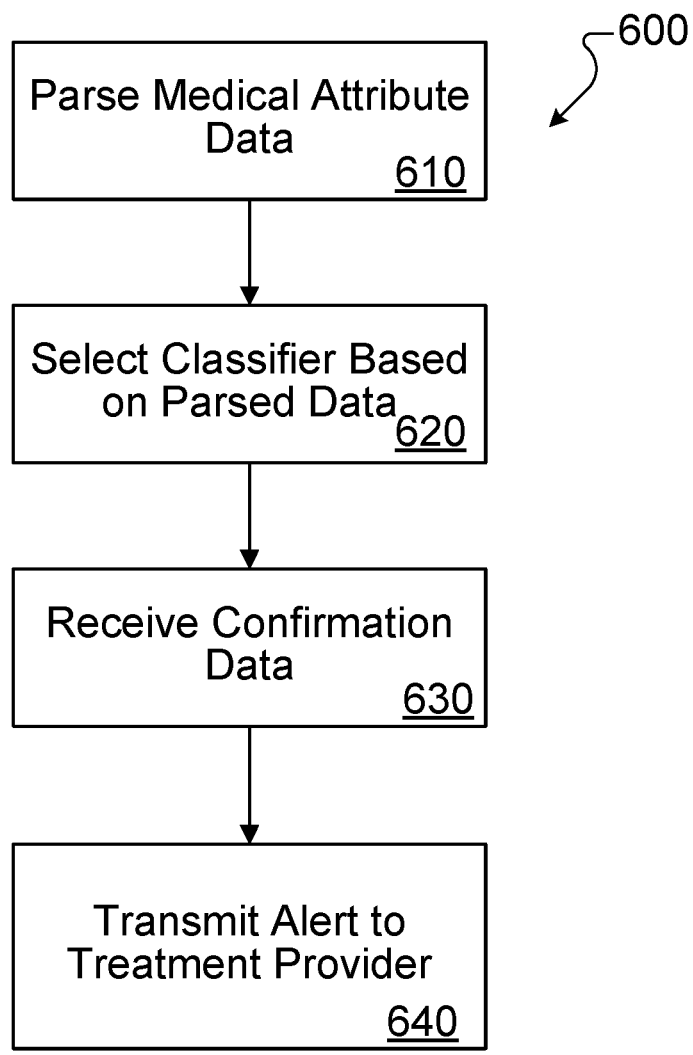
FIG. 6 represents a flow diagram of a process for monitoring and remediating treatment risks by a classification system.

FIG. 6 shows a flow diagram 600 of example processes for the classification system 100. At step 610, the classification system parses one or more items of structured medical data to retrieve values of respective fields of the one or more items of structured medical data, the one or more retrieved values representing a set of medical attributes. At step 620, the classification system 620 selects, from the memory a classifier based at least one of the attributes in the set and further applies the classifier to the set of attributes to classify the one or more items of structured medical data into a particular risk profile that includes a plurality of risk factors. At step 630, the classification system receives medical confirmation data that confirms one or more of the risk factors of the risk profile. At step 640, the classification system transmits an alert that specifies confirmation of the one or more of the risk factors.

Figure 7:
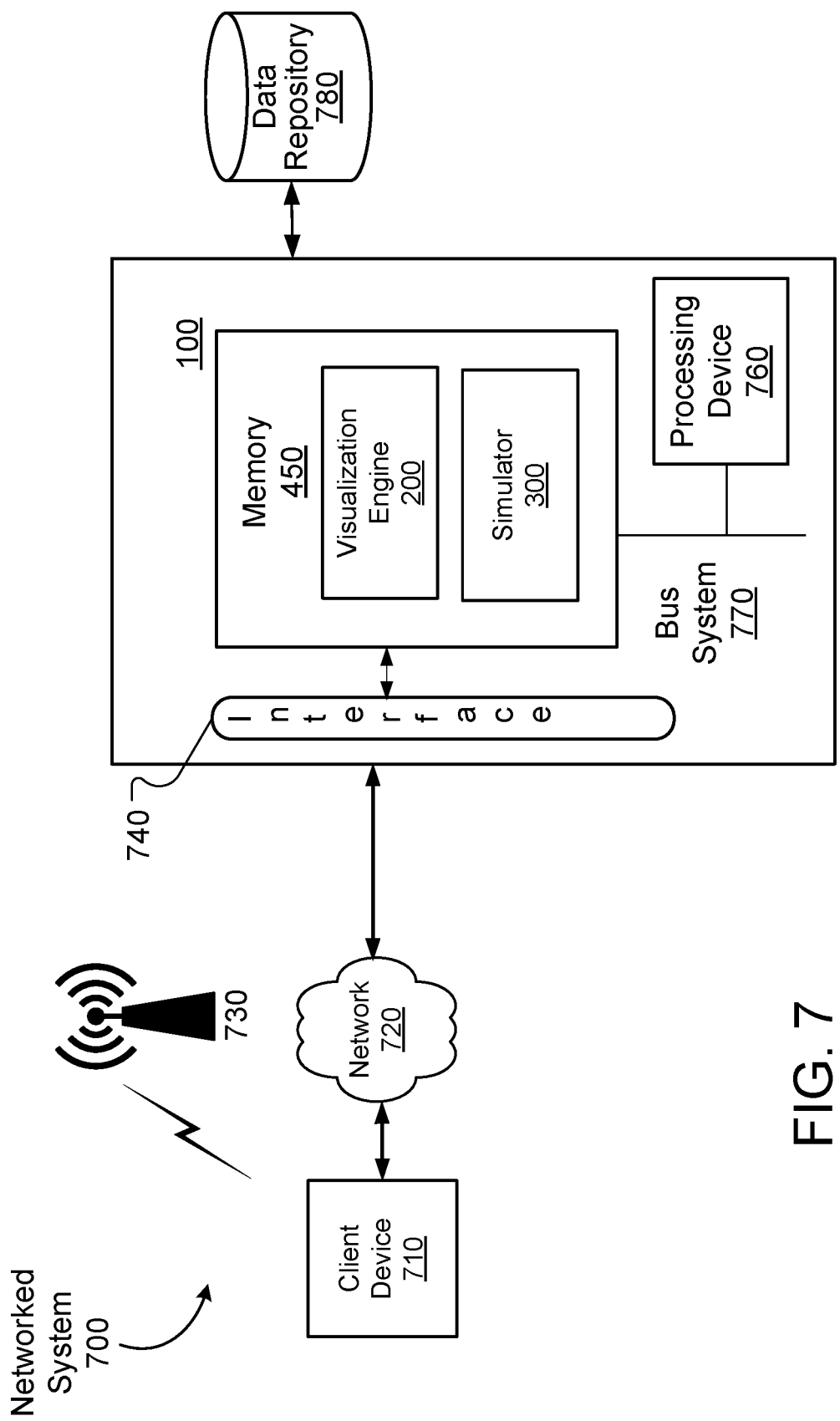
FIG. 7 shows a computing system of the classification system.

FIG. 7 is a block diagram showing examples of components of networked system 700. Client device 710 can be any sort of computing device capable of taking input from a user and communicating over network 720 with classification system 100 and/or with other client devices. Client device 710 can be a mobile device, a desktop computer, a laptop, a cell phone, a personal data assistant ("PDA"), a server, an embedded computing system, a mobile device and so forth, and can run the classification module 125 and user interface module 110. In some examples, networked system 700 is an execution environment. In other examples, the classification system 100 is the execution environment.

Each of the client device 105, the classification module 125, and other computer-based systems described herein can be a variety of computing devices capable of receiving data and running one or more services. In an example, classification system 100 can include a server, a distributed computing system, a desktop computer, a laptop, a cell phone, a rack-mounted server, and the like. Classification system 100 can be a single server or a group of servers that are at a same position or at different positions (i.e., locations). System and client device 710 can run programs having a client-server relationship to each other. Although distinct modules are shown in the figures, in some examples, client and server programs can run on the same device.

The classification system 100 can receive data from wireless devices 730 and/or client device 710 through input/output (I/O) interface 740. I/O interface 740 can be a type of interface capable of receiving data over a network, including, e.g., an Ethernet interface, a wireless networking interface, a fiber-optic networking interface, a modem, and so forth. System 730 also includes a processing device 760 and memory 750. A bus system 770, including, for example, a data bus and a motherboard, can be used to establish and to control data communication between the components of classification system 100.

Processing device 760 can include one or more microprocessors. Generally, processing device 760 can include an appropriate processor and/or logic that is capable of receiving and storing data, and of communicating over a network (not shown). Memory 750 can include a hard drive and a random access memory storage device, including, e.g., a dynamic random access memory, or other types of non-transitory machine-readable storage devices. Memory 750 stores computer programs, such as the visualization engine 200, that are executable by processing device 760. These computer programs include a simulator 300 for implementing the operations and/or the techniques described herein. The simulator 300 can be implemented in software running on a computer device, hardware or a combination of software and hardware. A data repository 780 can store data, such as behavior logs, etc.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible program carrier for execution by, or to control the operation of, a processing device. Alternatively, or in addition, the program instructions can be encoded on a propagated signal that is an artificially generated signal, e.g., a machine-generated electrical, optical, or electromagnetic signal that is generated to encode information for transmission to suitable receiver apparatus for execution by a processing device. A machine-readable medium can be a machine-readable storage device, a machine-readable storage substrate, a random or serial access memory device, or a combination of one or more of them.

The term "processing device" encompasses apparatuses, devices, and machines for processing information, including by way of example a programmable processor, a computer, or multiple processors or computers. The apparatus can include special purpose logic circuitry, e.g., an FPGA (field programmable gate array) or an ASIC (application-specific integrated circuit) or RISC (reduced instruction set circuit). The apparatus can also include, in addition to hardware, code that creates an execution environment for the computer program in question, e.g., code that constitutes processor firmware, a protocol stack, an information base management system, an operating system, or a combination of one or more of them.

A computer program (which may also be referred to as a program, software, a software application, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or information (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input information and generating output. The processes and logic flows can also be performed by, and apparatus can also be implemented as, special purpose logic circuitry, e.g., an FPGA (field programmable gate array) or an ASIC (application-specific integrated circuit) or RISC.

Computers suitable for the execution of a computer program include, by way of example, general or special purpose microprocessors or both, or any other kind of central processing unit. Generally, a central processing unit will receive instructions and information from a read-only memory or a random access memory or both. The essential elements of a computer are a central processing unit for performing or executing instructions and one or more memory devices for storing instructions and information. Generally, a computer will also include, or be operatively coupled to receive information from or transfer information to, or both, one or more mass storage devices for storing information, e.g., magnetic, magneto-optical disks, or optical disks. However, a computer need not have such devices. Moreover, a computer can be embedded in another device, e.g., a mobile telephone, a smartphone or a tablet, a touch-screen device or surface, a personal digital assistant (PDA), a mobile audio or video player, a game console, a Global Positioning System (GPS) receiver, or a portable storage device (e.g., a universal serial bus (USB) flash drive), to name just a few.

Although for clarity of exposition various parts of this disclosure refer to a smart phone, those parts should be read as describing, in place of a smart phone, other wireless handheld devices which run software. Similarly, for clarity of exposition various parts of this disclosure refer to an app, but those parts should be read as describing, in place of app, other form of software or computer systems to perform some or all of the methods described herein. Similarly, for clarity of exposition various parts of this disclosure refer to preterm birth risk, but those parts should be read as describing, in place of preterm birth risk, other risks, such as low birth weight, which can be detected and/or reduced as described herein.

Computer-readable media suitable for storing computer program instructions and information include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and (Blue Ray) DVD-ROM disks. The processor and the memory can be supplemented by, or incorporated in, special purpose logic circuitry.

Methods performed by software typically operate on data (e.g., training data, application data) that can be stored in remotely. The software may be, but need not be, stored in the same memory or memories that store such data. Intermediate and final results of executing the software can also be stored on the same memory or different memories.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back-end component, e.g., as an information server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital information communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In another example, the server can be in the cloud via cloud computing services.

While this specification includes many specific implementation details, these should not be construed as limitations on the scope of any of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of embodiments of the classification system have been described. Nevertheless, it will be understood that various modifications may be made without departing from the spirit and scope of the classification system. Accordingly, other embodiments are within the scope of the following claims.

What is claimed is:

1. A structured medical data classification system for classifying structured medical data for prophylaxis of adverse pregnancy outcomes for a patient, with each item of structured medical data comprising one or more fields and one or more values in the one or more fields, comprising:
   at least one processor; and
   a memory in communication with the processor, the memory storing instructions that, when executed by the at least one processor, cause the at least one processor to perform operations comprising:
      training a machine learning classifier to classify the structured medical data into a risk profile that represents one or more risk factors for adverse pregnancy outcomes for the patient, the machine learning classifier being trained with training data from one or more other patients, the training data representing a known pregnancy outcome for the one or more other patients;
      determining that a checkpoint in a treatment timeline for monitoring the adverse pregnancy outcomes for the patient is reached;
      based on the checkpoint in the treatment timeline, updating the risk profile of the patient, the risk profile representing the one or more risk factors for adverse pregnancy outcomes for the patient, wherein updating the risk profile comprises:
         parsing one or more items of structured medical data to retrieve values of respective fields of the one or more items of structured medical data, the one or more retrieved values representing a set of medical attributes describing a medical status of the patient;
         wherein the set of medical attributes comprise at least one of a depression scale, violence scale, a vitamin use, existence of substance abuse, demographic data, an access of a user interface of a tracking application, an appointment attendance, a mood, and a stress level of the patient, data describing vaginal flora, presence of a sexually transmitted disease, lower genital tract inflammatory milieu during pregnancy, pregnancy history, race, marital status, maternal periconceptional nutritional status, pregnancy nutritional status, approximate blood alcohol level, a count of fetal kicks or contractions, or a smoking status of the patient;

accessing the memory and selecting, from the memory, the machine learning classifier based at least one of the medical attributes in the set, the machine learning classifier being pre-trained using the training data;

applying the machine learning classifier to the set of medical attributes to classify the one or more items of structured medical data into the risk profile that represents the one or more risk factors;

generating a user interface that presents one or more controls for input of medical confirmation data, being measured at the checkpoint in the treatment timeline, that confirms one or more of the risk factors of the risk profile;

transmitting, over one or more communication protocols and to a remote medical device, an alert that specifies confirmation of the one or more of the risk factors, wherein pre-training the machine learning classifier reduces or eliminates a latency of transmitting the alert caused by training the machine learning classifier; and updating a medical status of the patient based on an outcome of treatment provided to the patient in response to the transmitted alert;

wherein the machine learning classifier is generated by performing graph-learning comprising:

receiving data representing medical attributes of a plurality of patients, wherein the medical attributes comprise the set of medical attributes of the patient;

classifying each of the patients of the plurality of patients into one or more health outcomes; and generating a graph of nodes and edges, wherein a node represents a medical attribute, and wherein an edge represents a causal relationship between connected medical attributes;

wherein the patient is not included in the plurality of patients, and wherein the graph-learning further comprises:

generating a set of decision trees by performing, for each decision tree of the set, operations comprising:

selecting a subset of the plurality of patients by sampling from the plurality of patients; and selecting a medical attribute of the subset of the plurality of patients that splits the subset of the plurality of patients into two groups of approximately equal size;

determining, using the set of decision trees, a classification of the set of medical attributes for the patient; and generating the risk profile of the patient based on the classification of the set of medical attributes for the patient.

2. The system of claim 1, wherein the alert comprises an answer to a question that is customized to address a risk factor of the risk profile of the patient.

3. The system of claim 1, wherein the one or more risk factors include a risk of an adverse pregnancy outcome for the patient.

4. The system of claim 1, further comprising:
updating the machine learning classifier based on a reported outcome of treatment provided to the patient in response to the transmitted alert.

5. The system of claim 1, further comprising:
executing logic to test the data representing the medical attributes of the plurality of patients, the test being configured to identify a general dependence or conditional dependence between or among the medical attributes, the test comprising:

testing a marginal independence of each pair of the medical attributes using a linear model;

when the linear model does not detect a correlation between a given pair of medical attributes, applying one or more transformations to each of the medical attributes of the pair of medical attributes to determine whether the correlation exists between the given pair of medical attributes; and generating the machine learning classifier based on determining whether correlations exist between each pair of the medical attributes, the determined correlations providing an indication of the one or more of the risk factors of the risk profile.

6. The system of claim 1, wherein the one or more risk factors include a risk of suicide for the patient.

7. The system of claim 1, further comprising a wearable electronic device and wherein receiving the set of medical attributes comprises receiving physiological data from the wearable electronic device.

8. The system of claim 1, wherein the user interface displays one or more controls enabling the patient to request immediate medical attention.

9. The system of claim 8, wherein the immediate medical attention comprises receiving transportation to a medical facility.

10. The system of claim 1, wherein the confirmation data comprises answers to one or more medical questions.

11. The system of claim 1, wherein the set of medical attributes comprises physiological data.

12. The system of claim 1, wherein the machine learning classifier is trained with labeled attributes describing medical statuses of patients.

13. The system of claim 1, wherein the operations further comprise:

detecting, based on applying the machine learning classifier to the set of medical attributes, a chronic medical condition in the patient, the chronic medical condition comprising at least one of diabetes, an existing substance abuse by the patient, depression, a mental health condition, a sleep problem, or a domestic violence condition.

14. A method for classifying structured medical data for prophylaxis of adverse pregnancy outcomes for a patient, with each item of structured medical data comprising one or more fields and one or more values in the one or more fields, the method comprising:

training a machine learning classifier to classify the structured medical data into a risk profile that represents one or more risk factors for adverse pregnancy outcomes for the patient, the machine learning classifier being trained with training data from one or more other patients, the training data representing a known pregnancy outcome for the one or more other patients;

determining that a checkpoint in a treatment timeline for monitoring the adverse pregnancy outcomes for the patient is reached;

based on the checkpoint in the treatment timeline, updating the risk profile of the patient, the risk profile representing the one or more risk factors for adverse pregnancy outcomes for the patient, wherein updating the risk profile comprises:

parsing one or more items of structured medical data to retrieve values of respective fields of the one or more items of structured medical data, the one or more retrieved values representing a set of medical attributes describing a medical status of the patient;

wherein the set of medical attributes comprise at least one of a depression scale, violence scale, a vitamin use, existence of substance abuse, demographic data, an access of a user interface of a tracking application, an appointment attendance, a mood, and a stress level of the patient, data describing vaginal flora, presence of a sexually transmitted disease, lower genital tract inflammatory milieu during pregnancy, pregnancy history, race, marital status, maternal periconceptional nutritional status, pregnancy nutritional status, approximate blood alcohol level, a count of fetal kicks or contractions, or a smoking status of the patient;

selecting, from a memory of a computing device, the machine learning classifier based at least one of the medical attributes in the set, the machine learning classifier being pre-trained using the training data from the one or more other patients;

applying the machine learning classifier to the set of medical attributes to classify the one or more items of structured medical data into the risk profile that represents the one or more risk factors;

generating a user interface that renders one or more controls for input of medical confirmation data, being measured at the checkpoint in the treatment timeline, that confirms one or more of the risk factors of the risk profile;

transmitting, over one or more communication protocols and to a remote medical device, an alert that specifies confirmation of the one or more of the risk factors, wherein pre-training the machine learning classifier reduces or eliminates a latency of transmitting the alert caused by training the machine learning classifier; and updating a medical status of the patient based on an outcome of treatment provided to the patient in response to the transmitted alert wherein the machine learning classifier is generated by performing graph-learning comprising:

receiving data representing medical attributes of a plurality of patients, wherein the medical attributes comprise the set of medical attributes of the patient;

classifying each of the patients of the plurality of patients into one or more health outcomes; and generating a graph of nodes and edges, wherein a node represents a medical attribute, and wherein an edge represents a causal relationship between connected medical attributes;

wherein the patient is not included in the plurality of patients, and wherein the graph-learning further comprises:

generating a set of decision trees by performing, for each decision tree of the set, operations comprising:

selecting a subset of the plurality of patients by sampling from the plurality of patients; and selecting a medical attribute of the subset of the plurality of patients that splits the subset of the plurality of patients into two groups of approximately equal size;

determining, using the set of decision trees, a classification of the set of medical attributes for the patient; and generating the risk profile of the patient based on the classification of the set of medical attributes for the patient.

15. The method of claim 14, wherein the alert comprises an answer to a question that is customized to address a risk factor of the risk profile of the patient.

16. A non-transitory computer-readable medium for classifying structured medical data for prophylaxis of adverse pregnancy outcomes for a patient, with each item of structured medical data comprising one or more fields and one or more values in the one or more fields, the non-transitory computer readable medium configured to cause one or more processing devices to perform operations comprising:

training a machine learning classifier to classify the structured medical data into a risk profile that represents one or more risk factors for adverse pregnancy outcomes for the patient, the machine learning classifier being trained with training data from one or more other patients, the training data representing a known pregnancy outcome for the one or more other patients;

determining that a checkpoint in a treatment timeline for monitoring the adverse pregnancy outcomes for the patient is reached;

based on the checkpoint in the treatment timeline, updating the risk profile of the patient, the risk profile representing the one or more risk factors for adverse pregnancy outcomes for the patient, wherein updating the risk profile comprises:

parsing one or more items of structured medical data to retrieve values of respective fields of the one or more items of structured medical data, the one or more retrieved values representing a set of medical attributes describing a medical status of the patient;

wherein the set of medical attributes comprise at least one of a depression scale, violence scale, a vitamin use, existence of substance abuse, demographic data, an access of a user interface of a tracking application, an appointment attendance, a mood, and a stress level of the patient, data describing vaginal flora, presence of a sexually transmitted disease, lower genital tract inflammatory milieu during pregnancy, pregnancy history, race, marital status, maternal periconceptional nutritional status, pregnancy nutritional status, approximate blood alcohol level, a count of fetal kicks or contractions, or a smoking status of the patient;

selecting, from a memory of a computing device, the machine learning classifier based at least one of the medical attributes in the set, the machine learning classifier being pre-trained using the training data from the one or more other patients;

applying the machine learning classifier to the set of medical attributes to classify the one or more items of structured medical data into the risk profile that represents the one or more risk factors;

generating a user interface that renders one or more controls for input of medical confirmation data, being measured at the checkpoint in the treatment timeline, that confirms one or more of the risk factors of the risk profile;

transmitting, over one or more communication protocols and to a remote medical device, an alert that specifies confirmation of the one or more of the risk factors, wherein pre-training the machine learning classifier reduces or eliminates a latency of transmitting the alert caused by training the machine learning classifier; and updating a medical status of the patient based on an outcome of treatment provided to the patient in response to the transmitted alert wherein the machine learning classifier is generated by performing graph-learning comprising:

receiving data representing medical attributes of a plurality of patients, wherein the medical attributes comprise the set of medical attributes of the patient;

classifying each of the patients of the plurality of patients into one or more health outcomes; and generating a graph of nodes and edges, wherein a node represents a medical attribute, and wherein an edge represents a causal relationship between connected medical attributes;

wherein the patient is not included in the plurality of patients, and wherein the graph-learning further comprises:

generating a set of decision trees by performing, for each decision tree of the set, operations comprising:

selecting a subset of the plurality of patients by sampling from the plurality of patients; and selecting a medical attribute of the subset of the plurality of patients that splits the subset of the plurality of patients into two groups of approximately equal size;

determining, using the set of decision trees, a classification of the set of medical attributes for the patient; and generating the risk profile of the patient based on the classification of the set of medical attributes for the patient.

17. A wireless handheld device for analyzing and classifying structured medical data for prophylaxis of adverse pregnancy outcomes for a patient, the device comprising:

a user interface;
a transceiver;
a processor; and
a memory in communication with the processor, the memory storing an application which is configured to cause the processor, when executing the application, to perform operations including:

causing training of a machine learning classifier to classify the structured medical data into a risk profile that represents one or more risk factors for adverse pregnancy outcomes for the patient, the machine learning classifier being trained with training data from one or more other patients, the data representing a known pregnancy outcome for the one or more other patients;

determining that a checkpoint in a treatment timeline for monitoring the adverse pregnancy outcomes for the patient is reached;

based on the checkpoint in the treatment timeline, updating the risk profile of the patient, the risk profile representing the one or more risk factors for adverse pregnancy outcomes for the patient, wherein updating the risk profile comprises:

parsing one or more electronic health records to retrieve values of respective fields of the electronic health records, the retrieved values associated with one or more tests performed during a pregnancy and describing a medical status of the patient;

wherein the retrieved values are associated with at least one of a depression scale, violence scale, a vitamin use, existence of substance abuse, demographic data, an access of a user interface of a tracking application, an appointment attendance, a mood, and a stress level of the patient, data describing vaginal flora, presence of a sexually transmitted disease, lower genital tract inflammatory milieu during pregnancy, pregnancy history, race, marital status, maternal periconceptional nutritional status, pregnancy nutritional status, approximate blood alcohol level, a count of fetal kicks or contractions, or a smoking status of the patient;

accessing the memory and selecting, from the memory, the machine learning classifier, the machine learning classifier being configured to detect one or more statistical dependencies between two or more of the retrieved values associated with the one or more tests performed during the pregnancy, the one or more dependencies including a non-linear dependency, the machine learning classifier being pre-trained using the training data from one or more other patients;

applying the machine learning classifier to the values of the respective fields of the electronic health records to classify the patient into a risk profile that that represents the one or more risk factors for adverse pregnancy outcomes;

causing the user interface to present one or more controls for input of answers to questions generated in response to classifying the patient into the risk profile, the answers being measured at the checkpoint in the treatment timeline and confirming one or more of the risk factors of the risk profile;

causing the transceiver to transmit, via a mobile network, an alert that specifies confirmation of the one or more of the risk factors for an adverse pregnancy outcome, wherein pre-training the machine learning classifier reduces or eliminates a latency of transmitting the alert caused by training the machine learning classifier;

updating a medical status of the patient based on an outcome of treatment provided to the patient in response to the transmitted alert;

executing logic to test the data representing the medical attributes of the plurality of patients, the test being configured to identify a general dependence or conditional dependence between or among the medical attributes, the test comprising:

testing a marginal independence of each pair of the medical attributes using a linear model;

when the linear model does not detect a correlation between a given pair of medical attributes, applying one or more transformations to each of the medical attributes of the pair of medical attributes to determine whether the correlation exists between the given pair of medical attributes; and generating the machine learning classifier based on determining whether correlations exist between each pair of the medical attributes, the determined correlations providing an indication of the one or more of the risk factors of the risk profile.

* * * * *

UNITED STATES PATENT AND TRADEMARK OFFICE
CERTIFICATE OF CORRECTION

PATENT NO. : 11,682,495 B2  
APPLICATION NO. : 16/341736  
DATED : June 20, 2023  
INVENTOR(S) : Krishnamurti et al.

Page 1 of 1

It is certified that error appears in the above-identified patent and that said Letters Patent is hereby corrected as shown below:

In the Claims

Column 28, Line 44, Claim 17, delete "that that" and insert -- that --

Signed and Sealed this  
Ninth Day of December, 2025

John A. Squires  
*Director of the United States Patent and Trademark Office*